(12) United States Patent
Liu et al.

(10) Patent No.: US 7,838,667 B2
(45) Date of Patent: Nov. 23, 2010

(54) GRAFTING POLYMERIZATION OF GUAR AND OTHER POLYSACCHARIDES BY ELECTRON BEAMS

(75) Inventors: Leo Zhaoqing Liu, Lawrenceville, NJ (US); Christian Priou, Charbonnieres-les-Bains (FR)

(73) Assignee: Rhodia, Inc., Cranbury, NJ (US)

( * ) Notice: Subject to any disclaimer, the term of this patent is extended or adjusted under 35 U.S.C. 154(b) by 0 days.

(21) Appl. No.: 10/607,079

(22) Filed: Jun. 25, 2003

(65) Prior Publication Data
US 2004/0072947 A1 Apr. 15, 2004

Related U.S. Application Data

(60) Provisional application No. 60/391,689, filed on Jun. 25, 2002, provisional application No. 60/405,547, filed on Aug. 23, 2002.

(51) Int. Cl.
C08B 37/00 (2006.01)
C07H 1/08 (2006.01)
C08B 1/00 (2006.01)

(52) U.S. Cl. ............... 536/114; 536/56; 536/84; 536/124; 536/128

(58) Field of Classification Search ............ 536/56, 536/84, 114, 124, 128
See application file for complete search history.

(56) References Cited

U.S. PATENT DOCUMENTS

| 3,461,052 | A | * | 8/1969 | Restaino et al. ............. 522/117 |
| 3,518,176 | A |   | 6/1970 | Reyes et al. |
| 3,522,158 | A | * | 7/1970 | Garnett et al. ............. 522/89 |
| 4,831,097 | A | * | 5/1989 | Chuang et al. ............. 527/312 |
| 4,973,680 | A | * | 11/1990 | Billmers ............. 536/58 |
| 5,223,171 | A | * | 6/1993 | Jost et al. ............. 510/471 |
| 6,939,536 | B2 | * | 9/2005 | Chen et al. ............. 424/70.1 |
| 2001/0020090 | A1 | * | 9/2001 | Becker et al. ............. 536/88 |

FOREIGN PATENT DOCUMENTS

| DE | 4207465 | 9/1993 |
| DE | 19627259 | 1/1998 |

* cited by examiner

Primary Examiner—Shaojia Anna Jiang
Assistant Examiner—Everett White
(74) Attorney, Agent, or Firm—John S. Child, Jr.

(57) ABSTRACT

A method of grafting galactomannan-type polysaccharide polymers, preferably guar, to a functional group by irradiation with high energy electron beams in the presence of an unsaturated monomer-compressing the described functional group. The method may include the depolymerization of the grafted polymer to a pre-selected low molecular weight. The preferred galactomannans for treatment according to this method are guar gum, guar splits and hydroxypropyl guar. In a preferred embodiment the guar gum is also depolymerized, preferably to a molecular weight of below about 700,000 Daltons, and most preferably to a molecular weight of between about 100,000 Daltons to about 250,000 Daltons. The depolymerized guar most preferably has a polydispersity of less than about 3.0 and is useful in oil well fracturing to enhance oil production.

10 Claims, 1 Drawing Sheet

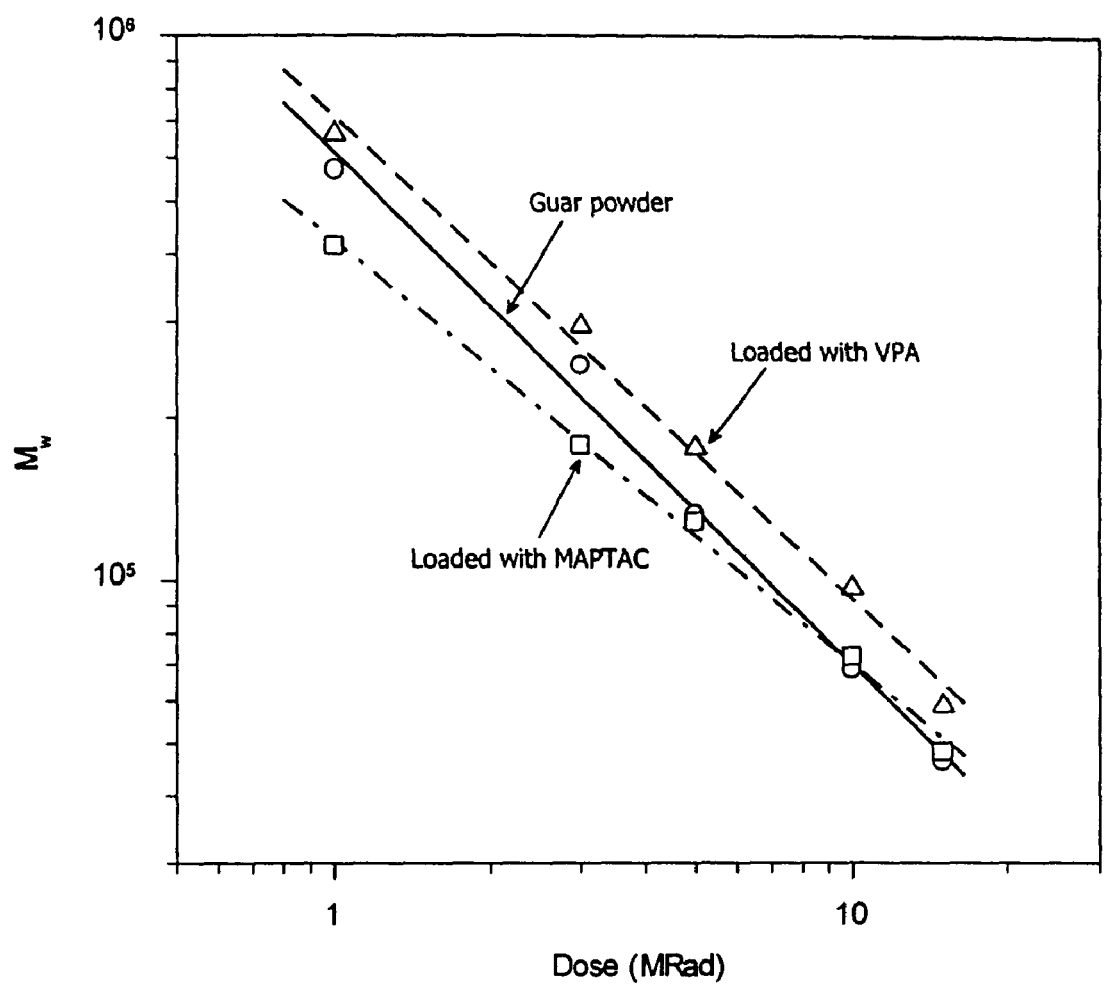
Figure 1. Depolymerization of Guar.

GRAFTING POLYMERIZATION OF GUAR AND OTHER POLYSACCHARIDES BY ELECTRON BEAMS

CROSS-REFERENCE TO RELATED APPLICATIONS

This Application claims the benefit under 35 U.S.C. §119 of U.S. Provisional Application No. 60/391,689, filed Jun. 25, 2002, and of U.S. Provisional Application No. 60/405,547, filed Aug. 23, 2002.

FIELD OF THE INVENTION

The invention relates to a method for chemically modifying polysaccharide polymers, in particular water dispersible and/or soluble polysaccharides and galactomannans such as guar gum, by irradiation using high energy electron beams. The method of the invention is effective for grafting onto polysaccharides various functional groups, in order to impart certain predetermined properties or characteristics to the polymers produced thereby.

BACKGROUND OF THE INVENTION

Polysaccharides, in particular galactomannans such as guar, have a variety of uses. Guar in the form of gum is used primarily in food and personal care products for its thickening property. The gum has five to eight times the thickening power of starch. Guar gum is also used as a fracturing aid in oil production.

Guar gum is the mucilage found in the seed of the leguminous plant *Cyamopsis tetragonolobus*. The seeds are composed of a pair of tough non-brittle endosperm sections, hereinafter referred to as guar splits. Guar splits contain guar gum but are tough and extremely difficult to grind into a powder form for recovery of the gum. After processing, native guar gum is obtained in the form of a yellow powder and has a molecular weight of between about 2,000,000 Daltons and 5,000,000 Daltons.

In certain applications, such as in food products, cosmetics, and shampoos, it would be desirable to use a polysaccharide, in particular a galactomannan such as guar gum, that is modified by grafting thereto a functional group such as a vinyl monomer, or other material. It would also be desirable that the grafted polysaccharide, galactomannan or guar gum be dispersible and/or soluble in water and have a molecular weight lower than the ungrafted polysaccharide, galactomannan or guar.

It was reported that guar was grafted with acrylamide in the presence of Cerium (IV). Deshmukh, S. R.; Singh, R. P. J. Appl. Polym. Sci. (1987) 33, 1963. Guar was grafted with acrylonitrite under gamma radiation to yield a water superabsorbent. Lokhande, H. T. et al. J. Appl. Polym. Sci. (1992), 45, 2031-20-36. The use of an initiator such as cerium (IV) is not industrially feasible due to the toxicity and the cost. Although the gamma irradiation grafting polymerization provides a way to produce the grafted guar, the irradiation itself requires expensive containment and a radioactive source.

It was reported in Romanian Patent 66503 that cellulositic products with improved properties (especially resistance to microorganisms) were prepared by grafting fibrous cellulositic materials (e.g. cotton fabric) with monomers (e.g. methylmethacrylate, vinyl chloride or vinylidone chloride at 10-25° C. with accelerated electrons of 500-3000 MeV at 108-109 rads and a total dose of 1-3 Mrads and a current strength of 20-25 A. The fibrous cellulose materials were given a preliminary treatment with NaOH at 90° C. for 60 minutes.

High energy electron beams have been used to graft vinyl monomers to polysaccharides, such as starch and cellulose. Olivier, A. et al. Biomacromolecules (2001), 2, 1260-1266; Ruckert, D. et al. J. Appl. Polym. Sci. (1999), 73 409-417; Yamagishi, H. et al. J. Membr. Sci. (1993), 85, 71-81; Ratzsch, M. et al. Acta Polym. Sci. (1999), 41, 620-7. There are numerous other articles describing how to graft vinyl monomers to polysaccharides, mainly cellulose and starch, in order to make plastic composite materials, and/or to give a property to the solid surfaces, such as fiber or membrane. Insofar as is known, however, it has not previously been proposed to modify water dispersible and/or soluble polysaccharides such as galactomannans or water dispersible and/or soluble cellulose derivatives with vinyl monomers with the intention of producing new products that can be used preferably in liquid compositions. Moreover, none of the graft polysaccharides previously reported was described as having a molecular weight lower than the original polysaccharides, while controlling the molecular weight during the grafting.

SUMMARY OF THE INVENTION

It is an objective of the invention to graft functional groups by means of unsaturated monomers bearing such groups, e.g., vinyl monomers, to polysaccharides, in particular galactomannans such as guar, to form a product having pre-selected properties or characteristics.

It is another objective of the invention that the modified polysaccharides may be depolymerized to a predetermined molecular weight range to enhance the usefulness of the grafted polymer.

It is also an objective of the invention to provide a method for grafting polysaccharides, galactomannans, and in particular guar gum, to functional groups, which reduces the formation of impurities in the final product.

It is a further objective of the invention to provide a polysaccharide grafting and depolymerization method that can be carried out entirely at approximately room temperature, and without the use of radioactive materials as a source of depolymerizing radiation.

It is another objective of the invention to produce grafted water-soluble or water dispersible polysaccharides, which would be used as additives in liquid formulations through electron beam irradiation with vinyl monomers or polymers.

It is yet a further objective of the invention to produce a depolymerized grafted guar gum having a pre-selected molecular weight and polydispersity.

These and other objectives can be achieved by the method of the invention, in which polysaccharides, in particular modified water dispersible and/or soluble celluloses such as hydroxyalkyl cellulose, galactomannans such as guar gum powder, guar splits, cationic guar, nonionic guar, water swollen guar splits, hydroxypropyl guar powder, xanthan and xanthan gum are exposed to high energy electron beam irradiation, in the presence of at least one unsaturated monomer having various functional groups, to thereby graft the functional groups to the polysaccharide. According to the invention, a galactomannan such as guar gum is modified by having functional groups grafted thereto, which imparts predetermined properties to the modified product. Furthermore, guar gum, which has a molecular weight of at least 2,000,000 Daltons, is depolymerized in the process to a lower pre-selected molecular weight. This lower pre-selected weight is preferably no more than about 700,000 Daltons, preferably less than about 500,000 Daltons, and more preferably, less than 300,000 Daltons. The method of the invention is also applicable to the modification and depolymerization of other galactomannans and polysaccharides.

Also within the scope of the invention is the grafted depolymerized polysaccharide, in particular grafted polysaccharides dispersible and/or soluble in water such as modified cellulose, and guar gum grafted to functional groups, which is produced according to the method described herein. These grafted water dispersible and/or soluble polysaccharides are intended to be used particularly in food applications, cosmetics and other personal care products, pharmaceuticals and other industrial applications, such as flowable pesticides, liquid feed supplements, shampoo compositions, cleaners, ceramics and coatings.

The type and dosage of the high energy electron beams employed in the practice of this invention will vary, depending on the type of polysaccharide polymer being treated, the extent of chemical modification and molecular weight reduction desired and the rate of depolymerization desired. With respect to the grafting and depolymerization of guar gum, the dosage of electron beam radiation to which the guar gum is exposed will vary preferably from about 0.5 Mrad about 20 Mrad, but dosages of electron beam radiation that are lower and higher than this preferred range may also be used.

BRIEF DESCRIPTION OF THE DRAWING

FIG. 1 is a graph showing a decrease in the molecular weight of guar gum powder, a guar gum grafted with methyacrylamidopropyltrimethylammonium chloride (MAPTAC) and guar gum grafted with vinyl phosphonic acid (henceforth "VPA") as a function of exposure to increasing radiation doses from a high energy electron beam.

DETAILED DESCRIPTION OF THE INVENTION

A. Polysaccharides

The term "polysaccharide" as used herein refers to a polymer having repeated saccharide units, including starch, polydextrose, lingocellulose, cellulose and derivatives of these (e.g., methylcellulose, ethylcellulose, carboxymethylcellulose, hydroxyethylcellulose, cellulose acetate, cellulose acetate butyrate, cellulose acetate propionate, starch and amylose derivatives, amylopectin and its derivatives and other chemically and physically modified starches) and the like.

B. Galactomannans

Galactomannans are polysaccharides consisting mainly of the monosaccharides mannose and galactose. The mannose-elements form a chain consisting of many hundreds of (1→4)-β-D-mannopyranosyl-residues, with 1→6 linked α-D-galactopyranosyl-residues at varying distances, dependent on the plant of origin. The galactomannans of the present invention may be obtained from numerous sources. Such sources include guar gum, guar splits, locust bean gum and tara gum, as further described below. Additionally, the galactomannans may also be obtained by classical synthetic routes or may be obtained by chemical modification of naturally occurring galactomannans.

1. Guar Gum

Guar gum, often called "guar flour" after grinding, refers to the mucilage found in the seed of the leguminous plant *Cyamopsis tetragonolobus*. The water soluble fraction (85%) is called "guaran," which consists of linear chains of (1→4)-.beta.-D mannopyranosyl units—with .alpha.-D-galactopyranosyl units attached by (1→6) linkages. The ratio of D-galactose to D-mannose in guaran is about 1:2. Guar gum may take the form of a whitish powder which is dispersible in hot or cold water. Guar gum may be obtained, for example, from Rhodia, Inc. (Cranbury, N.J.), Hercules, Inc. (Wilmington, Del.) and TIC Gum, Inc. (Belcamp, Md.).

2. Guar Splits

Guar seeds are composed of a pair of tough, non-brittle endosperm sections, hereafter referred to as "guar splits," between which is sandwiched the brittle embryo (germ). After dehulling, the seeds are split, the germ (43-47% of the seed) is removed by screening, and the splits are ground. The gum is present in the splits contained in tiny cells having a water-insoluble cell wall. The gum in these cells is rather slowly dispersible in water, and accordingly it is desirable to disrupt the cell wall as well as to obtain a fine particle size.

The splits are reported to contain about 78-82% galactomannan polysaccharide and minor amounts of some proteinaceous material, inorganic salts, water-insoluble gum, and cell membranes, as well as some residual seedcoat and embryo. They are tough and extremely difficult to grind.

3. Locust Bean Gum

Locust bean gum or carob bean gum is the refined endosperm of the seed of the carob tree, *Ceratonia siliqua*. The ratio of galactose to mannose for this type of gum is about 1:4. Cultivation of the carob tree is old and well known in the art of gum production. This type of gum is commercially available and may be obtained from TIC Gum, Inc. (Bekamp, Md.) and Rhodia, Inc. (Cranbury, N.J.).

4. Tara Gum

Tara gum is derived from the refined seed gum of the tara tree. The ratio of galactose to mannose is about 1:3. Tara gum is not produced in the United States commercially, but the gum may be obtained from various sources outside the United States.

C. Modified Cellulose

Modified celluloses are celluloses containing at least one functional group such as an hydroxy group or hydroxycarboxyl group or hydroxyalkyl group (i.e., hydroxymethyl-, hydroxyethyl-, hydroxypropyl- or hydroxybutyl).

D. Modified Galactomannans

Other galactomannans of interest are the modified galactomannans, including carboxymethyl guar, carboxymethylhydroxypropyl guar, cationic hydroxpropyl guar, hydroxyalkyl guar, including hydroxyethyl guar, hydroxypropyl guar, hydroxybutyl guar and higher hydroxylalkyl guars, carboxylalkyl guars, including carboxymethyl guar, carboxylpropyl guar, carboxybutyl guar, and higher alkyl carboxy guars, the hydroxyethylated, hydroxypropylated and carboxymethylated derivative of Guaran, the hydroxethylated and carboxymethylated derivatives of Carubin and the hydroxypropylated and carboxymethylated derivatives of Cassia-Gum. A preferred modified galactomannan is a hydroxypropyl guar with low molecular substitution e.g., less than 0.6.

E. Xanthan

Xanthans of interest are xanthan gum and gel. Xanthan gum is a polysaccharide gum produced by *Xathomonas campestris*. Xanthan gum contains D-glucose, D-mannose, D-glucuronic acid as the main hexose units and also contains pyruvate acid and is partially acetylated.

According to the present invention, polysaccharide polymers, in particular galactomannans such as solid guar gum, modified cellulose and xanthan gum, are mixed with unsaturated compounds containing functional groups, preferably derivatives of polymerizable vinyl compounds, with the objective that the functional group-containing compound is grafted onto the polymer. The resulting mixture is irradiated with high energy electron beams. The irradiation causes the mixture to form a modified water dispersible and/or soluble polysaccharide, in which the functional group is grafted to the polysaccharide structure, and to a pre-selected lower molecular weight. The amount and period of such irradiation used is dependent on the particular material being treated. The type and amount of irradiation used may vary in relation to the particular polymer species which is processed according to the invention and the functionalized unsaturated compound used for grafting. The method of this invention is applicable to a wide variety of polysaccharides, but it is particularly applicable to water dispersible and/or soluble polysaccharides, galactomannans and modified galactomannans. The method is particularly useful for the modification and depolymerization of guar gum and its derivatives in the form of a powder or splits. Preferred functional groups to be grafted onto the polymer are provided by vinyl monomers having such groups, e.g., carboxylate, sulfonate, phosphonate and quaternary ammonium groups.

Typical graft monomers, mixed with the polysaccharides to provide the functional groups grafted onto the polysaccharide are as follows:

TABLE 1

Properties Imported to Products by Functional Groups

| Graft Monomers | Functional Group |
|---|---|
| Methacrylic Acid | Carboxylate |
| Acrylamidodimethyl propane sulfuric acid ("AMPS") | Sulfonate |
| Vinyl Phosphonic Acid ("VPA") | Phosphonate |
| Methacrylamidopropyltrimethylammonium chloride ("MAPTAC") | Quarternary Ammonium |

The polysaccharide polymer treated according to this invention is in the solid phase prior to, and during, treatment. The term "solid phase" includes powders, granules, flakes, particles, and the like. Initially, the polymer and unsaturated monomer having a functional group are mixed together.

The irradiation is applied directly to the polymer unsaturated monomer mixture in the solid phase, preferably as the polymer passes on trays on a production line continuous belt. According to this invention, the solid polymer to be modified, with or without depolymerization, is placed in a tray up to a thickness that promotes complete penetration of the solid material by the high energy electron beams. Polydispersity is reduced if all of the material is penetrated by the electron beam. The layer of solid material exposed to the high energy electron beam should have a substantially uniform thickness if a low polydispersity is desired. The mixture of the polymer and the unsaturated functional group-containing compound to be irradiated may be deposited in a suitable container and covered with a radiation pervious thin plastic film for safety purposes. This covering is not essential. The container is then carried, e.g., by a conveyor, through a radiation chamber. The mixture is irradiated with high energy electron beams at a specified dose rate, depending upon the extent of modification of the polymer to be obtained.

In irradiation processing, dose is defined as the amount of energy absorbed by the target material. Dosages are defined either in units of gray or mega rads. One kilogray is equal to 1,000 joules per kilogram. A mega rad is equal to 1,000,000 ergs per gram. Accordingly, one mega rad equals ten kilogray. The preferred dose is between about 0.5 and about 20 mega rads or about 5 to about 200 kilogray (kGy), which can be generated by a 4.5 MeV generator operating at 15 milliamps. Such generators are available from E-Beam Services, Inc., of Plainview, N.Y.

The dose rate is the amount of time required to provide the irradiation dosage needed to graft the polymer and functional group and optimally to depolymerize the polymer to the selected molecular weight. This rate has a direct bearing on the length of time it takes to deliver a given dose, and therefore the amount of time that the polymer is exposed to ionizing radiation. High power electron beams generate high irradiation doses rapidly. As set forth in Table 2, even a lower power (1 kW) e-beam will deliver a target irradiation dose 40 times faster than its equivalent gamma irradiation. The use of high power beams allows a much higher production rate of grafted depolymerized galactomannan.

TABLE 2

Comparison of Dose Rates Using Gamma Irradiation and Electron Beams

| | Gamma Process | E-BEAM Process |
|---|---|---|
| Target dose | 20 kGy | 20 kGy |
| Dose rate (process-specific) | 10 kGy/hr | 400 kGy/hr |
| Time to deliver dose | 2 hrs (120 min) | 0.05 hrs (3 min) |

The high voltage electron beam irradiation of the polymer is carried out preferably at room temperature.

As noted above, the degree of depolymerization obtained in carrying out the method of the invention is influenced by the molecular weight of the original polymer being treated and the preselected molecular weight of the depolymerized product. Guar gum has a molecular weight of over 2,000,000 Daltons and generally between 2,000,000 Daltons and 5,000,000 Daltons. In the normal operation of this invention, the polymer will be depolymerized to a pre-selected value, preferably to below about 700,000 Daltons, more preferably to below about 500,000 Daltons and even more preferably to below about 300,000 Daltons.

In this invention, the irradiation of high-energy electrons is used to graft various functional group-containing vinyl monomers to polysaccharides, specifically guar and its derivatives, with or without depolymerizing them. By doing so, various properties, such as hydrophilicity/hydrophobicity, dispersibility and/or solubility in water and/or cationic characteristics (due to quaternary ammonium groups) or anionic characteristics (due to carboxylate, sulfonate, and phosphonate groups) are imparted to the natural polysaccharides. Therefore, the one-step irradiation process will not only depolymerize the polysaccharide, but also impart to the polymer various properties or characteristics to suit any specific applications.

As examples, guar powder was loaded in a weight ratio of 10:1 with methacrylamidopropyltrimethylammonium chloride (known as "MAPTAC") or vinyl phosphonic acid ("VPA") by suspending the polymer in a solution of the respective monomer in an appropriate solvent and then by evaporating the solvent in the vacuum. The monomer can also be loaded on the guar in a more economic way, such as spraying it in liquid form, which may be either undiluted or diluted in a suitable carrier. The molecular weight of the irradiated products was measured by gel permeation chromatograph. The weight average molecular weight is shown in FIG. 1.

Irradiation of the monomer-loaded guar test samples showed a slightly lower degree of depolymerization at the same dose than those without, an indication that grafting polymerization occurred. It was also observed that the grafted products contained less water-insoluble materials. NMR spectroscopy showed the isolated guar was grafted with either MAPTAC or vinylphosphonic acid.

A high energy electron beam generator of 1-10 MeV is preferred for practicing this invention because it penetrates deep into the materials, allowing a thicker layer of material to be irradiated. Higher than 10 MeV may be used, but this is not preferred because it may generate radioactivity from high-Z elements. A high voltage electron beam generator may be obtained from Electron Solutions Inc. and Science Research Laboratory, Somerville, Mass., Ion Beam Applications, Louvain-la-Neuve, Belgium, and The Titan Corporation, San Diego, Calif.

A low energy electron beam generator (150 kV-1 MeV) can also be used. The material will be irradiated as a layer as it passes through the beam; optionally, the irradiation is performed after the material has been mechanically ground to a powder. Such a generator is generally cheaper and does not require concrete shielding. A low voltage electron beam generator may be obtained from EZCure by Energy Sciences, Inc., Wilmington, Mass., Easy E-beam by Radiation Dynamics Inc., Edgewood, N.Y. and EB-ATP by Electron Solutions Inc., Somerville, Mass. This equipment is conventionally used primarily for surface irradiation curing.

Electron beams having low-energy (1.3 MeV) and high-power (>100 kW) can be used for guar grafting/depolymerization. The 100 kW power rating would be capable of grafting/depolymerizing 2400 kg/hour at a dose of 15 Mrad or 12,000 kg/hour at a dose of 3 Mrad.

The process of this invention will be useful as applied to graft/depolymerize other polygalactomannans (e.g. locust bean gum) or alpha-linked polyglucoses such as amylose and amylopectin.

As noted above, the depolymerized galactomannans are useful in food applications, cosmetics, pharmaceuticals and other industrial applications such as flowable pesticides, liquid feed supplements, shampoo compositions, cleaners, ceramics and coatings.

The following examples of the invention are provided for illustrative purposes only. It is not in any way intended to limit the invention.

Example 1

The following is an example of the graft polymerization of guar.

Guar powder was suspended in acetone, and then mixed with either vinyl phosphonic acid (VPA) or methacrylamidopropyltrimethylammonium chloride (MAPTAC) solution at a 10:1 ratio of guar to the respective monomer. The mixture was then dried in a vacuum and put into a plastic vial with its weight within the penetration range of the electron beam. The samples were then placed on a tray carried by an endless conveyor into a radiation chamber. The samples were irradiated by electron beam generated by 4.5 MeV generator operating at a 15 milliamps beam current at the top surface of the tray. The desired dose was obtained by adjusting the linear velocity of the conveyor.

After the irradiation, the molecular weight was analyzed by gel permeation chromatogram (column, Supelco Progel-TSK G3000PW$_{xl}$ and G6000PW$_{xl}$ in series; mobile phase, 55 mM Na$_2$SO$_4$, 0.02% NaN$_3$; flow rate, 0.6 ml/min; detector, Waters 410 Refractive Index; inj. Volume, 200 µl; temperature, 40° C.). The samples were dissolved in the mobile phase to give 0.025% solutions by weight. The calibration curve was generated using stachyose and two guar samples with molecular weights of 667, 58,000 and 2,000,000 Daltons.

The molecular weight distribution is set forth in Table 3. The molecular weight of the original sample was around 2,000,000 to 3,000,000. After the irradiation, the molecular weight decreased exponentially versus the irradiation dose. The polydispersity of the grafted guar/MAPTAC polymers varied from 2.91 to 3.45. The molecular weight can be predicted at a given dose according to FIG. 1. The guar powder loaded with either MAPTAC or VPA showed a decreasing rate of depolymerization.

The irradiated guar was dissolved in water at 1% concentration. The appearance and the amount of non-soluble were visually checked and compared with the irradiated non-grafted guar. The graft polymerization product generated a clearer solution and less precipitate after the solution settled down.

The grafted guar was isolated by washing out the corresponding homopolymer with methanol. The grafting of VPA or MAPTAC on the guar was confirmed by P-31 or proton NMR spectroscope respectively.

TABLE 3

Molecular Weight Distribution of Irradiated Guar

| Sample | Peak $M_p$ | Wt. Avg. $M_w$ | No. Avg. $M_n$ | Polydispersity $M_w/M_n$ |
|---|---|---|---|---|
| Guar powder, 0 rad | 2,960,000 | 2,860,000 | 1,200,000 | 2.37 |
| Guar powder, 1 M rad | 474,000 | 571,000 | 161,000 | 3.54 |
| Guar powder, 3 M rad | 196,000 | 249,000 | 78,900 | 3.16 |
| Guar powder, 5 M rad | 110,000 | 132,000 | 41,800 | 3.16 |
| Guar powder, 10 M rad | 59,900 | 68,100 | 21,700 | 3.13 |
| Guar powder, 15 M rad | 38,900 | 46,400 | 14,900 | 3.11 |
| Guar powder/MAPTAC 10/1, 1 M rad | 329,000 | 414,000 | 138,000 | 3.00 |
| Guar powder/MAPTAC 10/1, 3 M rad | 145,000 | 177,000 | 55,5000 | 3.19 |
| Guar powder/MAPTAC 10/1, 5 M rad | 111,000 | 128,000 | 41,000 | 3.13 |
| Guar powder/MAPTAC 10/1, 10 M rad | 69,100 | 72,100 | 20,900 | 3.45 |
| Guar powder/MAPTAC 10/1, 15 M rad | 40,300 | 48,200 | 16,600 | 2.91 |
| Guar powder/VPA 10/1, 1 M rad | 587,000 | 663,000 | 118,000 | 5.61 |
| Guar powder/VPA 10/1, 3 M rad | 223,000 | 294,000 | 59,000 | 4.99 |
| Guar powder/VPA 10/1, 5 M rad | 137,000 | 175,000 | 38,800 | 4.50 |
| Guar powder/VPA 10/1, 10 M rad | 90,600 | 96,600 | 21,100 | 4.57 |
| Guar powder/VPA 10/1, 15 M rad | 46,400 | 58,700 | 16,200 | 3.63 |

Example 2

Hydroxypropyl guar, available from Rhodia, Inc., in Cranbury, N.J., as Jaguar 8000, 50 parts was mixed with methacrylamidopropyltrimethylammonium chloride (MAPTAC, 50% in water), 15 parts and methanol 15 parts. The wet mixture was then dried in a vacuum oven at 30-40° C. The dried powder was then packed in a plastic bag with thickness less than 3 cm. The irradiation was done as described in Example 1 at a dose of 3.8 Mrad. The residual amount of non-reacted MAPTAC was analyzed by HPLC to be 0.39% in the sample (that is 97% conversion). The irradiated sample was then sprayed with 5 grams of 10% sodium metabisulfite solution in 1:1 water/methanol and then cured in a vacuum oven at 65-70° C. for two (2) hours. The residual monomer was analyzed again to be 440 ppm.

As the homopolymer of MAPTAC was found soluble in methanol, the MAPTAC-grafted guar was isolated by precipitation of an aqueous solution with methanol. Thus, the above metabisulfite treated guar 0.50 part was dissolved in 5.15 parts of water. The grafted guar was precipitated by adding methanol solution and dried. Proton NMR spectra showed roughly 9% of MAPTAC was on the isolated hydroxypropyl guar—that is, a grafting rate of more than 69%.

Example 3

The same procedure was used as in Example 2. Instead of MAPTAC, vinylphosphonic acid ("VPA") was the grafting monomer. About 2.3% VPA was attached to the isolated hydroxypropyl guar, a grafting rate greater than 20%.

Example 4

Hydroxyethylcellulose, available from Dow as Cellosize HEC QP 100M-H was sprayed with 50% MAPTAC solution at the ratios of the active components shown in Table 4, and then thoroughly mixed. The MAPTAC-swollen cellulose was then air-dried and ground into powder for easy handling. The irradiation and the post-treatment were done according to the procedure described in Example 2 with the dose shown in Table 4. The residual MAPTAC was measured by HPLC analysis after the irradiation (Table 4) and after further treatment (Table 5). The molecular weight was determined for selective samples (Table 6). Little or no homopolymer of MAPTAC was detected by the GPC analysis. The grafted polymer was isolated from aqueous methanol solution by precipitating with acetone. Colloid titration of the isolated polymer indicated more than 85% of the MAPTAC was attached to hydroxyethylcellulose.

TABLE 4

Percentage of MAPTAC after Irradiation

| | Dsage (Mrad) | | | | | |
|---|---|---|---|---|---|---|
| | 0.5 | 1 | 3 | 5 | 10 | 20 |
| HEC/MAPTAC: | | | | | | |
| 85/15 | 2.18 | 0.76 | 1.66 | 0.060 | 0.044 | 0.042 |
| 70/30 | 1.96 | 0.71 | 0.138 | 0.10 | 0.067 | 0.13 |
| 50/50 | 2.23 | 1.58 | 0.19 | 0.21 | 0.14 | 0.11 |

TABLE 5

Percentage of MAPTAC after Post-treatment

| | Dosage (Mrad) | | | | | |
|---|---|---|---|---|---|---|
| | 0.5 | 1 | 3 | 5 | 10 | 20 |
| HEC/MAPTAC: | | | | | | |
| 85/15 | 0.13 | 0.033 | 0.012 | ND | ND | 0.0027 |
| 70/30 | 0.021 | ND | ND | ND | ND | ND |
| 50/50 | 0.0113 | ND | ND | ND | ND | ND |

TABLE 6

GPC Molecular Weight ($M_w$) for Selective Samples

| | Irradiation Dosage (Mrad) | |
|---|---|---|
| | 0.5 | 10 |
| HEC/MAPTAC: | | |
| 85/15 | 552,000 | 119,000 |
| 70/30 | 488,000 | 101,000 |
| 50/50 | 310,000 | 103,000 |

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

What is claimed is:

1. A method for grafting an unsaturated monomer onto a guar comprising the steps of: (1) forming a mixture comprised of an unsaturated monomer having a functional group selected from quaternary ammonium and a water-soluble or water-dispersible guar; (2) drying the mixture and (3) irradiating the mixture with an amount of electron beam radiation sufficient to form an unsaturated monomer-water-soluble or water-dispersible guar graft copolymer, wherein the graft copolymer is depolymerized to a molecular weight lower than the molecular weight of the ungrafted guar, and the guar in the copolymer has a molecular weight of between 100,000 and 700,000 Daltons.

2. The method of claim 1, wherein the unsaturated monomer is a vinyl monomer having a quaternary ammonium group selected from methacrylamidopropyltrimethylammonium chloride.

3. The method of claim 1, wherein the guar is selected from the group consisting of guar gum and guar powder.

4. The method of claim 3, wherein the unsaturated monomer is a vinyl monomer having a quaternary ammonium group selected from methacrylamidopropyltrimethylammonium chloride.

5. The method of claim 1, wherein the guar is guar powder.

6. The method of claim 5, wherein the unsaturated monomer is a vinyl monomer having a quaternary ammonium group selected from methacrylamidopropyltrimethylammonium chloride.

7. The method of claim 1, wherein the guar is guar gum.

8. The method of claim 5, wherein the unsaturated monomer is a vinyl monomer having a quaternary ammonium group selected from methacrylamidopropyltrimethylammonium chloride.

9. A method for grafting an unsaturated monomer onto a guar comprising the steps of: (1) forming a mixture comprised of an unsaturated monomer having a functional group selected from quaternary ammonium and a water-soluble or water-dispersible guar; (2) drying the mixture in the air and (3) irradiating the mixture with an amount of electron beam radiation sufficient to form an unsaturated monomer-water-soluble or water-dispersible guar graft copolymer, wherein the graft copolymer is depolymerized to a molecular weight lower than the molecular weight of the ungrafted guar, and the guar in the copolymer has a molecular weight of between 100,000 and 700,000 Daltons.

10. A method for grafting an unsaturated monomer onto a guar comprising the steps of: (1) forming a mixture comprised of an unsaturated monomer having a functional group selected from quaternary ammonium and a water-soluble or water-dispersible guar; (2) drying the mixture in a vacuum and (3) irradiating the mixture with an amount of electron beam radiation sufficient to form an unsaturated monomer-water-soluble or water-dispersible guar graft copolymer, wherein the graft copolymer is depolymerized to a molecular weight lower than the molecular weight of the ungrafted guar, and the guar in the copolymer has a molecular weight of between 100,000 and 700,000 Daltons.

* * * * *